United States Patent
Nomura et al.

(10) Patent No.: US 10,377,686 B2
(45) Date of Patent: Aug. 13, 2019

(54) METHOD FOR PRODUCING 1-CHLORO-2,3,3,3-TETRAFLUOROPROPENE

(71) Applicant: AGC Inc., Chiyoda-ku (JP)

(72) Inventors: Shingo Nomura, Chiyoda-ku (JP); Hidekazu Okamoto, Chiyoda-ku (JP); Hirokazu Takagi, Chiyoda-ku (JP)

(73) Assignee: AGC Inc., Chiyoda-ku (JP)

( * ) Notice: Subject to any disclaimer, the term of this patent is extended or adjusted under 35 U.S.C. 154(b) by 0 days.

(21) Appl. No.: 16/105,513

(22) Filed: Aug. 20, 2018

(65) Prior Publication Data

US 2018/0354874 A1  Dec. 13, 2018

Related U.S. Application Data

(63) Continuation of application No. PCT/JP2017/007017, filed on Feb. 24, 2017.

(30) Foreign Application Priority Data

Feb. 25, 2016  (JP) ................. 2016-034101

(51) Int. Cl.
*B01J 21/18* (2006.01)
*B01J 23/42* (2006.01)
(Continued)

(52) U.S. Cl.
CPC ............... *C07C 17/23* (2013.01); *B01J 21/18* (2013.01); *B01J 23/42* (2013.01); *C07C 21/18* (2013.01); *C07B 61/00* (2013.01)

(58) Field of Classification Search
CPC ....... C07C 17/354; C07C 17/23; C07C 17/25; C07C 21/18; C07C 19/10; B01J 21/18; B01J 23/44; B01J 23/002; B01J 35/1023
See application file for complete search history.

(56) References Cited

U.S. PATENT DOCUMENTS

2010/0076231 A1    3/2010  Nappa et al.
2011/0319676 A1*  12/2011  Takagi ................ C07C 17/23
                                                                570/153
(Continued)

FOREIGN PATENT DOCUMENTS

CN    101535224    9/2009
CN    102947255    2/2013
(Continued)

OTHER PUBLICATIONS

International Search Report dated May 9, 2017 in PCT/JP2017/007017 filed Feb. 24, 2017 (with English Translation).
(Continued)

*Primary Examiner* — Jafar F Parsa
(74) *Attorney, Agent, or Firm* — Oblon, McClelland, Maier & Neustadt, L.L.P.

(57) ABSTRACT

An efficient method for producing 1-chloro-2,3,3,3-tetorafluoropropene from 1,1-dichloro-2,3,3,3-tetrafluoropropene is provided. The method produces 1-chloro-2,3,3,3-tetorafluoropropene by reducing 1,1-dichloro-2,3,3,3-tetrafluoropropene with fewer over-reduced by-products, such as 2,3,3,3-tetrafluoropropene and 1,1,1,2-tetrafluoropropane. In the method, 1,1-dichloro-2,3,3,3-tetrafluoropropene reacts with hydrogen in a gas phase in the presence of a palladium catalyst-carrying carrier, in which a palladium catalyst having a specific surface area of 40 m²/g or less is carried on the carrier.

9 Claims, 1 Drawing Sheet

(51) Int. Cl.
*C07B 61/00* (2006.01)
*C07C 17/23* (2006.01)
*C07C 21/18* (2006.01)

(56) References Cited

U.S. PATENT DOCUMENTS

2011/0319679 A1   12/2011  Takagi et al.
2015/0038749 A1   2/2015   Imura et al.
2015/0299072 A1*  10/2015  Sun ..................... C07C 17/354
                                                570/156

FOREIGN PATENT DOCUMENTS

| EP | 2 586 760 A1 | 5/2013 |
|---|---|---|
| JP | 2013-180964 | 9/2013 |
| JP | 2014-237627 | 12/2014 |
| JP | 5713019 | 5/2015 |
| TW | 200920722 | 5/2009 |
| TW | 201206566 A1 | 2/2012 |
| WO | WO 2008/054778 A2 | 5/2008 |
| WO | WO 2011/162340 A1 | 12/2011 |
| WO | WO 2011/162341 A1 | 12/2011 |
| WO | WO 2014/080868 A1 | 5/2014 |
| WO | WO 2016/031778 A1 | 3/2016 |
| WO | WO 2016/088779 A1 | 6/2016 |

OTHER PUBLICATIONS

Written Opinion dated May 9, 2017 in PCT/JP2017/007017 filed Feb. 24, 2017.

* cited by examiner

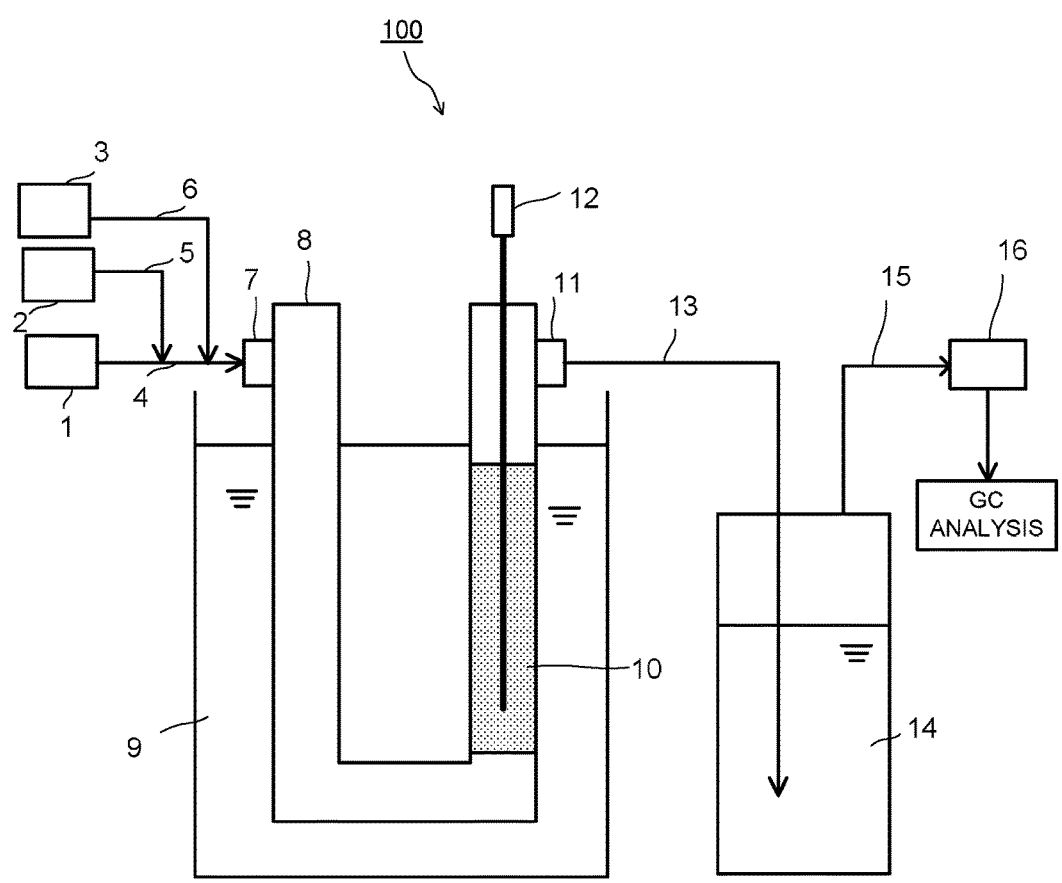

METHOD FOR PRODUCING 1-CHLORO-2,3,3,3-TETRAFLUOROPROPENE

CROSS-REFERENCE TO RELATED APPLICATIONS

This application is a continuation of prior International Application No. PCT/JP2017/007017, filed on Feb. 24, 2017 which is based upon and claims the benefit of priority from Japanese Patent Application No. 2016-034101, filed on Feb. 25, 2016; the entire contents of all of which are incorporated herein by reference.

FIELD

The present invention relates to a method for producing 1-chloro-2,3,3,3-tetrafluoropropene.

BACKGROUND 1-chloro-2,3,3,3-tetrafluoropropene ($CF_3CF=CHCl$, HCFO-1224yd, hereinafter, referred to also as 1224yd) is a compound having a small global warming potential and giving little load to a global environment, which is considered newly useful for the application in a cleaning agent, a refrigerant, a foaming agent, a solvent, and aerosol in place of chlorofluorocarbons such as 3,3-dichloro-1,1,1,2,2-pentafluoropropane ($CF_3$—$CF_2$—$CHCl_2$, HCFC-225ca) and 1,3-dichloro-1,1,2,2,3-pentafluoropropane ($CClF_2$—$CF_2$—$CClFH$, HCFC-225cb).

In this specification, as for a halogenated hydrocarbon, an abbreviation of a compound is given in a parenthesis after the name of the compound, and in this specification, the abbreviation is used as required instead of the name of the compound.

As 1224yd, there are a Z-isomer and an E-isomer being geometric isomers, which differ in a position of substituents on a double bond. In this specification, when the name of a compound or an abbreviation of a compound is used, it represents at least one kind selected from a Z-isomer and an E-isomer unless otherwise specified, and the name of a compound or an abbreviation of a compound with (E) or (Z) appended thereafter represents an E-isomer or a Z-isomer of the compound. For example, 1224yd(Z) and 1224yd(E) represent a Z-isomer and an E-isomer of 1224yd respectively.

As a production example of 1224yd, Patent Reference 1 (International Publication WO 2011/162341), for example, describes that, at the time of obtaining 2,3,3,3-tetrafluoropropene ($CF_3CF=CH_2$, HFO-1234yf) by reducing 1,1-dichloro-2,3,3,3-tetrafluoropropene ($CF_3CF=CCl_2$, CFO-1214ya, hereinafter, referred to also as 1214ya) through its reaction with hydrogen in the presence of a palladium catalyst, 1224yd is obtained as an intermediate. In Patent Reference 1, 1224yd obtained as the intermediate in the aforesaid reaction as well as 1214ya is used as a raw material compound of HFO-1234yf.

The Patent Reference 1 describes conditions and means for obtaining HFO-1234yf being a subject substance with a high yield in the method of reducing 1214ya through its reaction with hydrogen, but does not describe a method to efficiently obtain 1224yd which is classified as a by-product. That is, in the method of Patent Reference 1, 1224yd is slightly produced, but this method has a problem that a large amount of HFO-1234yf, which is an over-reduced product for 1224yd, and further 1,1,1,2-tetrafluoropropane ($CF_3CHFCH_3$, HFC-254eb), which is a reduced product of HFO-1234yf, are produced as by-products.

SUMMARY OF THE INVENTION

It is an object of the present invention to provide an efficient method for producing 1224yd, with fewer by-products such as HFO-1234yf and HFC-254eb which are over-reduced products, in a method of obtaining 1224yd by reducing 1214ya.

The present invention provides a method for producing 1224yd configured as follows.

[1] A method for producing 1-chloro-2,3,3,3-tetrafluoropropene (1224yd), comprising: reacting 1,1-dichloro-2,3,3,3-tetrafluoropropene (1214ya) with hydrogen in a gas phase in the presence of a palladium catalyst-carrying carrier in which a palladium catalyst having a specific surface area of 40 $m^2/g$ or less is carried on a carrier.

[2] The method according to [1], wherein the specific surface area is 6 to 33 $m^2/g$.

[3] The method according to [1], wherein the specific surface area is 6 to 20 $m^2/g$.

[4] The method according to [1], wherein the palladium catalyst contains palladium, and optionally a metal except palladium whose ratio to 100 parts by mass of palladium is 50 parts by mass or less.

[5] The method according to [1], wherein a mass ratio of the palladium catalyst to the carrier is 0.1 to 10% by mass.

[6] The method according to [1], wherein the palladium catalyst consists of palladium.

[7] The method according to [1], wherein the carrier is an activated carbon.

[8] The method according to [7], wherein the activated carbon is a palm shell activated carbon.

[9] The method according to [1], wherein a ratio of the number of moles of a molecule of the hydrogen to the number of moles of the 1214ya is 1.4 or less.

The production method of the present invention is a method to obtain 1224yd by reducing 1214ya for which a stable production method has been established, and is a method whose industrial implementation is easy and that is stably feasible. Further, according to the production method of 1224yd of the present invention, the high-reaction rate and high-selection rate production of 1224yd is possible, with fewer by-products such as HFO-1234yf and HFC-254eb which are over-reduced products.

BRIEF DESCRIPTION OF THE DRAWINGS

FIG. 1 is a schematic view illustrating a reaction device used in Examples.

DETAILED DESCRIPTION

The production method of 1224yd of the present invention is characterized in that 1214ya is made to react with hydrogen in a gas phase in the presence of a palladium catalyst-carrying carrier in which a palladium catalyst having a specific surface area of 40 $m^2/g$ or less is carried on a carrier. In this specification, hydrogen refers to a molecular hydrogen unless otherwise specified, and may be represented by $H_2$ as required. The reaction of 1214ya and the hydrogen according to the production method of 1224yd of the present invention is represented by the following formula (1).

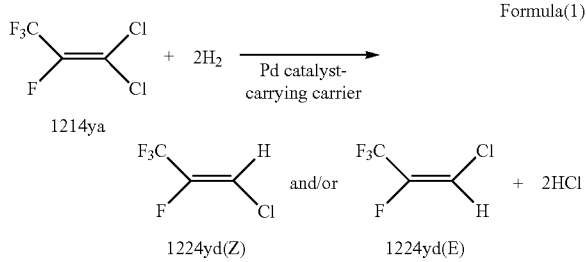

1224yd obtained by the production method of the present invention may be a mixture of a Z-isomer and an E-isomer, may be only the Z-isomer, or may be only the E-isomer. 1224yd not only has a high ratio of halogen which suppresses flammability but also has, in its molecule, a carbon-carbon double bond easily dissociated by OH radicals in the atmosphere, and thus is low in flammability, has a small influence on an ozone layer, and is small in GWP. Therefore, it has high usability for the application in a cleaning agent, a refrigerant, a foaming agent, a solvent, and aerosol.

<1214ya>

In the production method of 1224yd of the present invention, 1214ya is used as a raw material. 1214ya can be produced by a known method. A method to obtain 1214ya is not limited, and 1214ya can be produced by, for example, a method that brings HCFC-225ca into contact with an alkaline aqueous solution in the presence of a phase-transfer catalyst to cause its dehydrofluorination reaction, as represented by the following formula (2).

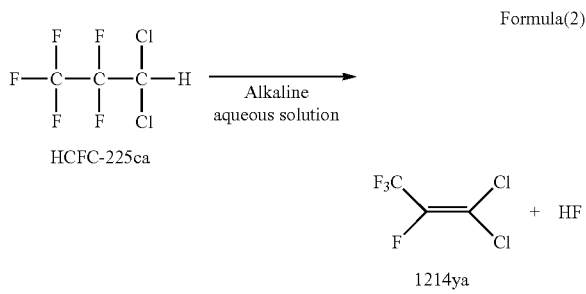

Note that HCFC-225ca used in the reaction of the formula (2) can be used in a state of a dichloropentafluoropropane (HCFC-225) isomer mixture including HCFC-225ca and an isomer thereof. In the case where the HCFC-225 isomer mixture is used, only HCFC-225ca in the HCFC-225 isomer mixture is selectively dehydrofluorinated by the phase-transfer catalyst. After the reaction, obtained 1214ya can be separated and recovered by a known method such as distillation. The phase-transfer catalyst is preferably tetrabutylammonium bromide (TBAB).

It is possible to produce the HCFC-225 isomer mixture including HCFC-225ca by, for example, making tetrafluoroethylene and dichlorofluoromethane react with each other in the presence of a catalyst such as aluminum chloride. The HCFC-225 isomer mixture obtained through the reaction contains HCFC-225ca and HCFC-225cb as main components, and besides contains small amounts of 2,2-dichloro-1,1,3,3,3-pentafluoropropane ($CHF_2CCl_2CF_3$, HCFC-225aa), 2,3-dichloro-1,1,2,3,3-pentafluoropropane ($CHF_2CClFCClF_2$, HCFC-225bb), and so on.

As the HCFC-225 isomer mixture including HCFC-225ca, a commercially available product may be used. Examples of the commercially available product include ASAHIKLIN AK225 (manufactured by Asahi Glass Co., Ltd., brand name, a mixture of 48 mol % HCFC-225ca and 52 mol % HCFC-225cb).

<Palladium Catalyst-Carrying Carrier>

In the production method of the present invention, 1214ya obtained by the above-described method or the like and the hydrogen are made to react in the gas phase in the presence of the palladium catalyst-carrying carrier in which the palladium catalyst having the specific surface area of 40 $m^2/g$ or less is carried on the carrier. Hereinafter, the palladium catalyst-carrying carrier in which the palladium catalyst having the specific surface area of 40 $m^2/g$ or less is carried on the carrier will be referred to as a palladium catalyst-carrying carrier (X).

The present invention enables the high-reaction rate and high-selection rate production of 1224yd, with fewer by-products such as HFO-1234yf and HFC-254eb which are over-reduced products, by causing the reaction of the above formula (1) in the presence of the palladium catalyst-carrying carrier (X).

In the present invention, the palladium catalyst in the palladium catalyst-carrying carrier (X) means a metal catalyst mainly containing palladium. Mainly containing palladium means that a ratio of metal except the palladium to 100 parts by mass of the palladium in the palladium catalyst is 50 parts by mass or less. The ratio of the metal except the palladium to 100 parts by mass of the palladium is preferably 30 parts by mass or less, and more preferably 10 parts by mass or less. It is especially preferable that the palladium catalyst contains no metal except the palladium, that is, the palladium catalyst consists of palladium because high catalytic activity is obtained therefrom.

Examples of the metal that the palladium catalyst may contain other than the palladium include: Group 8 elements such as iron, ruthenium, and osmium; Group 9 elements such as cobalt, rhodium, and iridium; Group 10 elements such as nickel and platinum; Group 11 elements such as gold, silver, and copper; rhenium, zinc, cadmium, tin, lead, antimony, and bismuth. Among these metals other than the palladium, one kind or two kinds or more may be contained. The palladium catalyst may be an alloy of the palladium and the other metal, or may be a mixture of the palladium and the other metal. Examples of the palladium alloy catalyst include a palladium and platinum alloy catalyst and a palladium and rhodium alloy catalyst. The palladium catalyst containing the metal other than the palladium is higher in catalytic durability than the palladium catalyst consisting of the palladium.

The specific surface area of the palladium catalyst used in the palladium catalyst-carrying carrier (X) is 40 $m^2/g$ or less. The specific surface area of the palladium catalyst is preferably 6 to 33 $m^2/g$, and more preferably 6 to 20 $m^2/g$ from a viewpoint of increasing production efficiency of 1224yd.

Note that, in this specification, the specific surface area of the palladium catalyst refers to a specific surface area measured by the following method using the palladium catalyst-carrying carrier (X) as a sample.

[Method of Measuring Specific Surface Area]

20 g of the palladium catalyst-carrying carrier (X) is weighed and filled in a column made of SUS316. As a pre-process, a helium gas is passed for thirty minutes, next a hydrogen gas for thirty minutes, and finally a helium gas for thirty minutes to the column under conditions of 40° C. and a gas flow rate of 300 mL/minute. Next, a CO gas is passed to the column at a constant volume pulse until adsorption reaches equilibrium, and a CO adsorption amount when the equilibrium is reached is estimated. Whether the adsorption has reached the equilibrium is confirmed by gas chromatography (TCD).

The specific surface area of the palladium catalyst (MSA) is calculated from the following formula (3).

$$MSA = (V \times a)/w \quad \text{Formula (3)}$$

w: mass (g) of the palladium catalyst in the palladium catalyst-carrying carrier (X)
V: CO adsorption amount (mL)
a: surface area of the palladium catalyst occupied per unit volume of CO at the time of the adsorption of CO (=4.35 m$^2$/mL)
w is calculated from a product of a mass (g) of the palladium catalyst-carrying carrier (X) and a content percentage (mass %) of the palladium catalyst.

In the production method of the present invention, the aforesaid palladium catalyst is used as the palladium catalyst-carrying carrier (X) carried on the carrier. Examples of the carrier include an activated carbon, and a metal oxide such as alumina, zirconia, silica, or titania. Among these, the activated carbon is preferable from a viewpoint of catalytic activity, durability, and reaction selectivity.

Examples of the activated carbon include those prepared using wood, charcoal, fruit shell, palm shell, peat, lignite, coal, or the like as a raw material, and that obtained from a plant raw material rather than a mineral raw material is more preferable, and a palm shell activated carbon is especially preferable. Examples of the shape of the activated carbon include a briquette of length about 2 to 5 mm, a pulverized carbon with an about a 4 to 50 mesh, and a granular carbon. Among them, the pulverized carbon with a 4 to 20 mesh or the briquette is preferable.

An amount of the palladium catalyst carried in the palladium catalyst-carrying carrier (X) is preferably 0.1 to 10% by mass, and more preferably 0.5 to 1% by mass to the carrier. When the amount of the carried palladium catalyst is equal to or more than the lower limit value, the reaction rate of 1214ya and the hydrogen improves. When the amount of the carried palladium catalyst is equal to or lower than the upper limit value, an excessive temperature increase of a catalyst layer (to be described later) due to reaction heat is easily inhibited and the production of the by-products is easily reduced.

As a method to make the palladium catalyst carried on the carrier, an ordinary method to make a metal catalyst carried on the carrier is usable without any special limitation. For example, in a case where the palladium catalyst consists of palladium and the carrier is an activated carbon, it is possible to obtain a palladium-carrying activated carbon by impregnating the activated carbon with an aqueous solution of a palladium salt such as palladium (II) chloride, palladium (II) nitrate, or tetraamminepalladium (II) chloride, precipitating the palladium salt to a surface of the activated carbon by drying, and reducing palladium ions in the palladium salt.

In the case where the palladium catalyst-carrying carrier (X) is fabricated by this method, it is possible to adjust the specific surface area of the palladium catalyst by heat-treating, in an inert gas, the carrier which is made to carry the palladium catalyst through the reduction as described above. In the above, by setting the temperature of the heat treatment to 400 to 800° C. and setting its duration to one to twenty hours, for instance, it is possible to obtain the palladium catalyst-carrying carrier (X) in which the specific surface area of the palladium catalyst is adjusted to the aforesaid range. Examples of the inert gas include nitrogen, carbon dioxide, helium, and argon.

<Production of 1224yd>

In the production method of the present invention, a specific example of a method to make 1214ya and the hydrogen react with each other in the gas phase in the presence of the palladium catalyst-carrying carrier (X) is a method that forms the catalyst layer filled with the palladium catalyst-carrying carrier (X) and introduces 1214ya and the hydrogen in a gaseous form to the catalyst layer.

In the present invention, the catalyst layer is typically formed by filling the palladium catalyst-carrying carrier (X) in a reactor. A filling density of the palladium catalyst-carrying carrier (X) in the catalyst layer is preferably 0.3 to 1 g/cm$^3$, and more preferably 0.4 to 0.8 g/cm$^3$. When the filling density of the palladium catalyst-carrying carrier (X) is equal to or more than the lower limit value, an amount of the palladium catalyst-carrying carrier (X) filled per unit volume is large, and thus an amount of the gas for the reaction can be increased, leading to productivity enhancement. When the filling density of the palladium catalyst-carrying carrier (X) is equal to or less than the upper limit value, the excessive temperature increase of the catalyst layer due to the reaction heat is easily inhibited, and the production of the by-products is easily decreased. The number of parts filled with the palladium catalyst-carrying carrier (X), that is, the number of the catalyst layers may be one, or may be two or more in the reactor.

To execute the production method of the present invention by using such a catalyst layer, the gaseous 1214ya and hydrogen are introduced from one side of the aforesaid catalyst layer. The gases of the introduced 1214ya and hydrogen react with each other in the gas phase while passing in the catalyst layer, resulting in the production of 1224yd. Then, a generation gas which contains 1224yd is discharged from a side of the catalyst layer, opposite to the side from which 1214ya and the hydrogen are introduced. Hereinafter, the production method of the present invention will be described, taking a case where the catalyst layer is used, as an example. In the catalyst layer, the side from which 1214ya and the hydrogen are introduced will be referred to as a "gas introduction part", and the side from which the generation gas is discharged will be referred to as a "gas discharge part".

A ratio of the hydrogen and 1214ya introduced to the catalyst layer is preferably such a ratio that a value of a ratio of the number of moles of the hydrogen to the number of moles of 1214ya (hereinafter, represented by a molar ratio ($H_2$/1214ya)) becomes 1.4 or less, from a viewpoint of decreasing the by-products such as HFO-1234yf and HFC-254eb which are over-reduced products. The smaller the molar ratio ($H_2$/1214ya), the more easily the by-products such as HFO-1234yf and HFC-254eb are decreased, and the molar ratio ($H_2$/1214ya) is more preferably 1.2 or less, and still more preferably 1.0 or less. Further, the molar ratio ($H_2$/1214ya) is preferably 0.2 or more, and more preferably 0.4 or more from a viewpoint of the yield of 1224yd.

In a case where the hydrogen is introduced in divided amounts as in a later-described method (A), it is similarly preferable that a ratio of the total amount of the hydrogen introduced to the catalyst layer and 1214ya introduced to the catalyst layer is such a ratio that the molar ratio ($H_2$/1214ya) becomes 1.4 or less, more preferably 1.2 or less, and still more preferably 1.0 or less. Further, the molar ratio ($H_2$/1214ya) is preferably 0.2 or more, and more preferably 0.4 or more.

In the production method of the present invention, because the reaction is a gas-phase reaction, a reaction temperature at which 1214ya is made to react with the hydrogen is set to a temperature higher than a dew point of a mixed gas of 1214ya and the hydrogen used in the reaction, or in the case where the inert gas is used, higher than a dew point of a mixed gas of 1214ya, the hydrogen, and the inert gas. Further, in the production method of the present invention, the reaction temperature is preferably 200° C. or lower, and more preferably 130° C. or lower from a viewpoint of inhibiting the production of the by-products.

The reaction temperature in the production method of the present invention is specifically a temperature of a reaction zone of the catalyst layer to be described below. In the production method of the present invention, by controlling the temperature of the reaction zone of the catalyst layer, that is, the maximum temperature of the catalyst layer, within the aforesaid range of the reaction temperature, it is possible to improve reactivity and inhibit the production of the by-products.

There is a problem that the temperature of the catalyst layer, even if initially set to the predetermined temperature, gradually becomes lower with the progress of the deterioration of the catalyst, resulting in a decrease in the reaction rate of the catalyzed reaction. Accordingly, it is preferable to perform an operation to keep the temperature of the catalyst layer at the predetermined temperature in order to maintain a high reaction rate. For example, in a case where the catalyst layer is heated from the outside by a heating medium or the like for the purpose of maintaining the temperature, gradually raising the temperature of the heating medium can prevent the temperature decrease of the catalyst layer.

Note that the temperature of the catalyst layer refers to the temperature at which the catalyst layer is kept by being heated from the outside or the like. Typically, 1214ya and the hydrogen react in a partial region of the catalyst layer, and the reaction zone (region where 1214ya and the hydrogen are reacting) has a higher temperature than the other region of the catalyst layer due to the generation of the reaction heat. As catalytic activity in this reaction zone decreases with time, the reaction zone usually gradually moves downstream in terms of a gas flow direction, from the vicinity of the gas introduction part. Further, since the high-temperature generation gas generated in the reaction zone flows in a region downstream of the reaction zone, the temperature in this region is usually higher than the temperature of the catalyst layer, and the temperature gradually decreases as the distance from the reaction zone increases. In the present invention, the temperature of the catalyst layer refers to the temperature in a region upstream of the reaction zone, that is, the temperature at which the catalyst layer is kept by being heated from the outside by the heating medium or the like.

Further, in the production method of the present invention, it is preferable to set the maximum temperature of the catalyst layer to the aforesaid upper limit value or lower of the reaction temperature by inhibiting an excessive temperature increase of the catalyst layer due to the reaction heat of 1214ya and the hydrogen. As described above, the temperature in the reaction zone where 1214ya and the hydrogen are reacting and in the region downstream thereof is higher than the temperature of the catalyst layer in the other region due to the reaction heat. The maximum temperature of the catalyst layer during the reaction refers to the maximum temperature of the catalyst layer region whose temperature has become higher than the temperature of the other region due to this reaction heat. An example of a method to measure the maximum temperature of the catalyst layer during the reaction is the following measuring method using an insertion-type thermometer.

In the reaction of 1214ya and the hydrogen in the catalyst layer, the catalyst near the gas introduction part to which they are introduced in the gaseous form first contributes to the reaction, and then when the catalyst near the gas introduction part deteriorates, the catalyst downstream of the gas introduction part contributes to the reaction, and in this manner, the reaction zone in the catalyst layer gradually moves toward the gas discharge side. That is, a part where the catalyst layer presents the maximum temperature moves as the reaction zone of 1214ya and the hydrogen moves, and therefore, by positioning a measurement part of the insertion-type thermometer at the gas introduction part of the catalyst layer in advance, and moving the measurement part as the reaction progresses, it is possible to measure the maximum temperature of the catalyst layer.

As a method to maintain the maximum temperature of the catalyst layer during the reaction at the aforesaid upper limit value or lower of the reaction temperature, the method that introduces the hydrogen in divided amounts to the catalyst layer (method (A)) is preferable from a viewpoint of easily maintaining high productivity while controlling the maximum temperature of the catalyst layer low. Introducing the hydrogen in divided amounts to a plurality of places of the catalyst layer makes it possible to disperse the reaction zones of the catalyst layer without changing an introduction amount of 1214ya, and accordingly prevents the concentration of the generation of the reaction heat at one place. This makes it possible to easily inhibit the local excessive heat generation of the catalyst layer without decreasing productivity.

Introducing the hydrogen in divided amounts means that 1214ya and part of a predetermined amount of the hydrogen used in this production method are introduced to the gas introduction part of the catalyst layer, and the rest of the hydrogen is introduced from at least one place between the gas introduction part and the gas discharge part of the catalyst layer. In other words, it means that the hydrogen is introduced from at least one place of the catalyst layer other than the gas introduction part, that is, from totally two places or more. In the divided introduction, the total amount of the hydrogen thus introduced from two places or more is the aforesaid predetermined amount of the hydrogen.

Specifically, amounts of 1214ya and the hydrogen which are introduced to the gas introduction part (located on the most upstream side in the catalyst layer in terms of the gas flow direction) of the catalyst layer are a part of the amount of the hydrogen introduced to the catalyst layer and the total amount of 1214ya. The rest of the hydrogen is introduced from a hydrogen introduction part to the catalyst layer located downstream in terms of the gas flow direction, the hydrogen is mixed to the gas (typically, the generation gas obtained after part of 1214ya reacts with the hydrogen) flowing in the catalyst layer at this introduction position, unreacted 1214ya reacts with the hydrogen in the catalyst layer downstream of this hydrogen introduction position, and the generation gas is discharged from the gas discharge part (located on the most downstream side in the catalyst layer in terms of the gas flow direction) of the catalyst layer.

Between the gas introduction part and the hydrogen introduction part on the most upstream side in terms of the gas flow direction, the hydrogen introduced from the gas introduction part preferably at least partly reacts with 1214ya. Further, the hydrogen introduction part on the most downstream side in terms of the gas flow direction is preferably provided at such a position that, in the catalyst layer between this hydrogen introduction part and the gas discharge part, the hydrogen introduced from this hydrogen introduction part and 1214ya can sufficiently react with each other.

In the method (A), the hydrogen may be introduced to two places in divided amounts, or may be introduced to three places or more in divided amounts, and from a viewpoint of enabling process simplification, the divided introduction from two places is preferable. In the divided introduction of the hydrogen to two places or more of the catalyst layer, amounts of the hydrogen introduced in the respective separate stages are preferably equal to each other because this facilitates maintaining the maximum temperature of the catalyst layer low.

In a case where there are two or more catalyst layers in the reactor, an example of the divided introduction of the hydrogen is a method that introduces part of the hydrogen to the most upstream (first-stage) catalyst layer together with 1214ya and introduces the rest of the hydrogen to the second-stage or subsequent-stage catalyst layers downstream of the first stage.

Further, a method to control the maximum temperature of the catalyst layer other than the method (A) is, for example, a method that makes an inert gas flow in the catalyst layer together with 1214ya and the hydrogen (method (B)). By making the inert gas flow and adjusting the concentration of 1214ya and the hydrogen flowing in the catalyst layer, it is possible to inhibit the excessive temperature increase of the catalyst layer due to the reaction heat. Alternatively, a diluent gas other than the inert gas is also usable instead of the inert gas or with the inert gas.

Examples of the inert gas include nitrogen, a rare gas (helium, argon, or the like), carbon dioxide, and fron gas inert to the hydrogenation reaction. Examples of the diluent gas other than the inert gas include hydrogen chloride.

An introduction amount of the inert gas to the catalyst layer is preferably 0.5 moles or more, and more preferably 1.0 mole or more, to 1 mole of 1214ya because this facilitates maintaining the maximum temperature of the catalyst layer low, facilitates reducing the production of the by-products, and facilitates inhibiting the deterioration of the catalyst. Further, from a viewpoint of the recovery of the inert gas, the introduction amount of the inert gas is preferably 10 moles or less, and more preferably 4 moles or less, to 1 mole of 1214ya.

In the method (B), because, in a reaction in a state where the raw materials are liquefied, the production of the by-products resulting from the excessive reduction of 1224yd increases to lower the yield of 1224yd, the temperature of the catalyst layer is preferably higher than the dew point of the aforesaid mixed gas. The temperature is more preferably higher than the dew point and lower than 200° C., and still more preferably higher than the dew point and equal to or lower than 150° C.

Another method to control the maximum temperature of the catalyst layer other than the method (A) and the method (B) is a method that sets the temperature of the catalyst layer further lower, with its lowest limit being the dew point of the mixed gas of 1214ya and the hydrogen used in the reaction, or, when the inert gas is used, with its lower limit being the dew point of the mixed gas of 1214ya, the hydrogen, and the inert gas (method (C)). Keeping the temperature of the catalyst layer low enables the quicker removal of the reaction heat, making it possible to inhibit the excessive temperature increase of the catalyst layer.

In the method (C), the temperature of the catalyst layer is preferably higher than the dew point of the aforesaid mixed gas because it is more advantageous in inhibiting the production of the by-products which are difficult to separate from 1224yd being the subject substance as the temperature of the catalyst layer is lower, and because, in the reaction in the state where the raw materials are liquefied, the production of the by-products resulting from the excessive reduction of 1224yd increases to lower the yield of 1224yd. The temperature of the catalyst layer is more preferably higher than the dew point and lower than 50° C., and still more preferably higher than the dew point and equal to or lower than 30° C.

For controlling the maximum temperature of the catalyst layer, it is preferable to use the method (A), the method (B), or the method (C) alone, or co-use two or three of these.

A reaction pressure is preferably a normal pressure from a viewpoint of handleability. A reaction time is preferably 0.4 to 400 seconds, more preferably 1 to 400 seconds, and most preferably 4 to 400 seconds. In the production method of the present invention, the reaction time is specifically a contact time of 1214ya with the palladium catalyst-carrying carrier (X). This contact time is calculated from a volume of 1214ya introduced to the reactor and a volume of the catalyst layer.

In the production method of the present invention, a linear velocity u of 1214ya in the catalyst layer, which is represented by the following formula (4), is preferably 0.1 to 100 cm/second, more preferably 0.1 to 30 cm/second, and most preferably 0.1 to 10 cm/second. The linear velocity u of 0.1 cm/second or more leads to an increase in productivity and makes it easy for 1214ya to uniformly flow in the catalyst layer. The linear velocity u of 100 cm/second or less leads to an improvement in the reaction rate of 1214ya and the hydrogen, and the linear velocity u of 30 cm/second or less facilitates controlling the temperature near a reaction site generating heat.

The linear velocity u is calculated by the following formula (4) from a gas amount of 1214ya introduced to the reactor and the volume of the catalyst layer.

$$u = (W/100) \times V/S \qquad \text{Formula (4)}$$

W: concentration (mol %) of 1214ya in the whole gas flowing in the catalyst layer V: flow rate ($cm^3$/second) of the whole gas flowing in the catalyst layer S: area ($cm^2$) of a cross section in a flow direction of the gas in the catalyst layer In the production method of the present invention, the gaseous component introduced to the catalyst layer may contain other components within a range not impairing the effect of the present invention, in addition to 1214ya, the hydrogen, and the optional components, namely, the inert gas and the diluent gas. An example of the other component is a component brought together with 1214ya as impurities when 1214ya is prepared.

An example of the reactor used in the production method of the present invention is a known reactor in which the catalyst layer can be formed by the catalyst-carrying carrier being filled. Examples of a material of the reactor include glass, iron, nickel, and an alloy containing any of these as a main component.

Besides 1224yd being the subject substance, the generation gas after the reaction contains the unreacted raw materials, HFO-1234yf, HFC-254eb, 1,1,1-trifluoropropane (CF$_3$CH$_2$CH$_3$, HFC-263fb), 3,3,3-trifluoropropene (CF$_3$CH=CH$_2$, HFO-1243zf) and the like, which are over-reduced products, and HCl.

It is possible to remove HCl contained in the generation gas by, for example, blowing the generation gas into an alkaline aqueous solution to neutralize it. Examples of an alkali used in the aforesaid alkaline aqueous solution include sodium hydroxide and potassium hydroxide. As a method to recover 1224yd from the generation gas, a known method such as fractionation is adoptable, for instance. The obtained 1224yd is typically the mixture of the E-isomer and the Z-isomer of 1224yd. If the separation of the E-isomer and the Z-isomer of 1224yd from the mixture is necessary, a separation and purification method such as distillation may be used.

According to the production method of the present invention described above, owing to the gas-phase reaction of 1214ya and the hydrogen in the presence of the palladium catalyst-carrying carrier in which the palladium catalyst having the specific surface area of 40 m$^2$/g or less is carried on the carrier, the by-products such as HFO-1234yf, HFC-254eb, HFC-263fb, and HFO-1243zf which are over-reduced products are decreased. As a result, an amount of 1224yd being the subject substance in the generation gas increases, enabling the efficient production of high-purity 1224yd. Further, since 1214ya used in the reaction is a compound for which a stable production method using easily available raw materials has been established, the production method of the present invention can be said as a method whose industrial implementation is easy and that is stably feasible.

EXAMPLES

Hereinafter, the present invention will be described in more detail by way of Examples and Comparative Examples. It should be noted that the present invention is not limited to the description below. Examples 1 to 4 are Examples and examples 5 to 8 are Comparative Examples.

First, palladium catalyst-carrying carriers used in the respective examples were prepared as follows. Palladium catalyst-carrying carries (X1) to (X3) are each the palladium catalyst-carrying carrier according to the present invention, and palladium catalyst-carrying carriers (Cf1) to (Cf3) are palladium catalyst-carrying carriers for Comparative Examples. Further, for preparing the palladium catalyst-carrying carriers, palladium-carrying activated carbon (manufactured by N.E. CHEMCAT CORPORATION; hereinafter, referred to as a "palladium-carrying activated carbon (A)") carrying a 0.5% by mass palladium catalyst consisting of palladium to 100% by mass palm shell activated carbon having a 4 to 8 mesh granular size was used. A specific surface area of the carried palladium catalyst (palladium) in the palladium-carrying activated carbon (A) as measured by the aforesaid specific surface area measuring method was 198 m$^2$/g.

Preparation Example 1

The palladium-carrying activated carbon (A) was heat-treated at 750° C. for ten hours in nitrogen, whereby the palladium catalyst-carrying carrier (X1) whose carried palladium had a specific surface area of 6 m$^2$/g was obtained.

Preparation Example 2

The palladium catalyst-carrying carrier (X2) whose carried palladium had a specific surface area of 20 m$^2$/g was obtained in the same manner as in the preparation example 1 except that the heat-treatment temperature in the preparation example 1 was changed to 600° C.

Preparation Example 3

The palladium catalyst-carrying carrier (X3) whose carried palladium had a specific surface area of 33 m$^2$/g was obtained in the same manner as in the preparation example 1 except that the heat-treatment temperature in the preparation example 1 was changed to 550° C.

Preparation Example 4

The palladium catalyst-carrying carrier (Cf1) whose carried palladium had a specific surface area of 41 m$^2$/g was obtained in the same manner as in the preparation example 1 except that the heat-treatment temperature in the preparation example 1 was changed to 500° C.

Preparation Example 5

The palladium catalyst-carrying carrier (Cf2) whose carried palladium had a specific surface area of 88 m$^2$/g was obtained in the same manner as in the preparation example 1 except that the heat-treatment temperature in the preparation example 1 was changed to 400° C.

Preparation Example 6

The palladium-carrying activated carbon (A) (the specific surface area of palladium was 198 m$^2$/g) was used as it was as the palladium catalyst-carrying carrier (Cf3).

Example 1

1224yd was produced by the aforesaid method (B) using a reaction device 100 whose schematic view is illustrated in FIG. 1. As illustrated in FIG. 1, the reaction device 100 includes one reaction tube 8 and an oil bath 9 in which the reaction tube 8 is immersed. As the reaction tube 8, a U-shaped reaction tube made of SUS304 with a 2.14 cm inside diameter and a 70 cm total length was used. The reaction tube 8 has, in its outlet 11 side, a catalyst layer 10 with a 40 cm height filled with the palladium catalyst-carrying carrier (X1) with a 0.73 g/cm$^3$ filling density prepared in the above.

The reaction device 100 further includes a 1214ya gas storage vessel 1, a hydrogen gas storage vessel 2, and a nitrogen gas storage vessel 3, and these vessels are connected to an inlet 7 of the reaction tube 8 through pipes 4, 5 and 6 respectively. A gas discharged from the outlet 11 of the reaction tube 8 is transferred to an alkaline cleaning tank 14 through a pipe 13, and after alkaline-cleaned, is recovered in a generation gas storage vessel 16 through a pipe 15. In the following description, the gas discharged from the outlet 11 of the reaction tube 8 will be referred to as "outlet gas", and the gas obtained after the outlet gas is alkaline-cleaned will be referred to as "generation gas".

First, the reaction tube 8 was immersed in the oil bath 9 whose temperature was adjusted to 100° C., with the catalyst layer 10 being completely immersed, thereby heating the catalyst layer 10 to 100° C. Next, a 1214ya gas, a hydrogen gas, and a nitrogen gas were made to flow in the reaction tube 8, and the discharged outlet gas was alkaline-cleaned, whereby the generation gas was obtained.

A contact time of the 1214ya gas with the palladium catalyst-carrying carrier (X1) filled in the catalyst layer 10 was set to twelve seconds, and a molar ratio (H$_2$/1214ya) which is a ratio of the number of moles of the total introduction amount of the hydrogen gas and the number of moles of the 1214ya gas introduced to the catalyst layer was set to 1.0. Further, a molar ratio ($N_2$/1214ya) which is a ratio of the number of moles of the total introduction amount of the nitrogen gas and the number of moles of the 1214ya gas introduced to the catalyst layer was set to 2.0. A linear velocity u of 1214ya was set to 0.8 cm/second.

Further, the maximum temperature (reaction temperature) of the catalyst layer 10 during the reaction as measured by an insertion-type thermometer 12 inserted into the catalyst layer was 88° C. When the 1214ya gas, the hydrogen gas, and the nitrogen gas flow in the catalyst layer, the temperature of the catalyst layer changes and may present a different temperature from the oil bath temperature. Actually, under such a state, the maximum temperature of the catalyst layer 10 was measured and was regarded as the aforesaid reaction temperature.

For the alkaline cleaning of the outlet gas, a 20% by mass aqueous sodium hydroxide solution whose temperature was 15° C. was used.

Example 2

A generation gas was obtained in the same manner as in the example 1 except that the palladium catalyst-carrying carrier (X1) was changed to the palladium catalyst-carrying carrier (X2) whose palladium had a specific surface area of 20 $m^2$/g. The maximum temperature of the catalyst layer 10 during the reaction as measured by the insertion-type thermometer 12 inserted into the catalyst layer was 123° C.

Example 3

A generation gas was obtained in the same manner as in the example 1 except that the palladium catalyst-carrying carrier (X1) was changed to the palladium catalyst-carrying carrier (X3) whose palladium had a specific surface area of 33 $m^2$/g and the temperature of the oil bath 9 was changed to 80° C. The maximum temperature of the catalyst layer 10 during the reaction as measured by the insertion-type thermometer 12 inserted into the catalyst layer was 146° C.

Example 4

A generation gas was obtained in the same manner as in the example 3 except that the temperature of the oil bath 9 was changed to 100° C. The maximum temperature of the catalyst layer 10 during the reaction as measured by the insertion-type thermometer 12 inserted into the catalyst layer was 189° C.

Example 5

A generation gas was obtained in the same manner as in the example 1 except that the palladium catalyst-carrying carrier (X1) was changed to the palladium catalyst-carrying carrier (Cf1) whose palladium had a specific surface area of 41 $m^2$/g and the temperature of the oil bath 9 was changed to 80° C. The maximum temperature of the catalyst layer 10 during the reaction as measured by the insertion-type thermometer 12 inserted into the catalyst layer was 161° C.

Example 6

A generation gas was obtained in the same manner as in the example 1 except that the palladium catalyst-carrying carrier (X1) was changed to the palladium catalyst-carrying carrier (Cf2) whose palladium had a specific surface area of 88 $m^2$/g. The maximum temperature of the catalyst layer 10 during the reaction as measured by the insertion-type thermometer 12 inserted into the catalyst layer was 159° C.

Example 7

A generation gas was obtained in the same manner as in the example 1 except that the palladium catalyst-carrying carrier (X1) was changed to the palladium catalyst-carrying carrier (Cf3) whose palladium had a specific surface area of 198 $m^2$/g and the temperature of the oil bath 9 was changed to 80° C. The maximum temperature of the catalyst layer 10 during the reaction as measured by the insertion-type thermometer 12 inserted into the catalyst layer was 165° C.

Example 8

A generation gas was obtained in the same manner as in the example 7 except that the temperature of the oil bath 9 was changed to 100° C. The maximum temperature of the catalyst layer 10 during the reaction as measured by the insertion-type thermometer 12 inserted into the catalyst layer was 185° C.

[Analysis Method]

The generation gases obtained in the respective examples were analyzed by gas chromatography (GC), and a selection rate X (unit: %) of 1214ya to 1224yd(Z) and its selection rate Y (unit: %) to 1224yd(E) were calculated by the following formulas (5) and (6) respectively.

$$X=[a/(a+b+c+d)]\times 100 \quad \text{Formula (5)}$$

$$Y=[b/(a+b+c+d)]\times 100 \quad \text{Formula (6)}$$

In the formulas (5) and (6), "a" represents the number of moles of 1224yd(Z), "b" represents the number of moles of 1224yd(E), "c" represents the number of moles of HFO-1234yf, and "d" represents the total number of moles of other over-reduced products (HFC-254eb, HFC-263fb, HFO-1243zf, and others).

Further, the yield of 1224yd (the Z-isomer and the E-isomer) was calculated by the following formula (7).

$$\text{Yield of } 1224yd(Z\text{-isomer and }E\text{-isomer})=[A\times(X+Y)]/100 \quad \text{Formula (7)}$$

In the formula (7), "A" represents the reaction rate of 1214ya.

Table 1 shows the analysis results together with the reaction conditions and so on. Further, Table 2 shows area ratios of the generation gases in the GC analysis in terms of molar ratio (unit:mol %). Note that the kinds of the palladium catalyst-carrying carriers in Table 1 are represented only by signs. In Table 2, E1 to E8 indicate Example 1 to Example 8.

TABLE 1

| | Example | | Example 1 | Example 2 | Example 3 | Example 4 | Example 5 | Example 6 | Example 7 | Example 8 |
|---|---|---|---|---|---|---|---|---|---|---|
| Pd catalyst-carrying carrier | Kind | | (X1) | (X2) | (X3) | (X3) | (Cf1) | (Cf2) | (Cf3) | (Cf3) |
| | Amount of carried Pd catalyst | Mass % | 0.5 | 0.5 | 0.5 | 0.5 | 0.5 | 0.5 | 0.5 | 0.5 |
| | Specific surface area of Pd catalyst | $m^2$/g | 6 | 20 | 33 | 33 | 41 | 88 | 198 | 198 |

TABLE 1-continued

| Example | | | Example 1 | Example 2 | Example 3 | Example 4 | Example 5 | Example 6 | Example 7 | Example 8 |
|---|---|---|---|---|---|---|---|---|---|---|
| Reaction condition | Maximum temperature of catalyst layer (reaction temperature) | °C. | 88 | 123 | 146 | 189 | 161 | 159 | 165 | 185 |
| | Temperature of oil bath | °C. | 100 | 100 | 80 | 100 | 80 | 100 | 80 | 100 |
| | Molar ratio ($H_2$/1214ya) | mol/mol | 1.0 | 1.0 | 1.0 | 1.0 | 1.0 | 1.0 | 1.0 | 1.0 |
| | Molar ratio ($N_2$/1214ya) | mol/mol | 2.0 | 2.0 | 2.0 | 2.0 | 2.0 | 2.0 | 2.0 | 2.0 |
| | Linear velocity of 1214ya | cm/sec | 0.8 | 0.8 | 0.8 | 0.8 | 0.8 | 0.8 | 0.8 | 0.8 |
| Analysis result of generation gas | Reaction rate of 1214ya [%] | | 57.5 | 57.1 | 56.6 | 55.1 | 55.0 | 55.9 | 49.3 | 49.9 |
| | Selection rate X to 1224yd(Z) [%] | | 9.7 | 8.4 | 10.8 | 6.8 | 10.2 | 5.7 | 4.8 | 4.6 |
| | Selection rate Y to 1224yd(E) [%] | | 15.3 | 15.1 | 12.3 | 16.6 | 5.8 | 5.3 | 6.3 | 6.9 |
| | X + Y [%] | | 25.0 | 23.5 | 23.1 | 23.4 | 16.0 | 11.0 | 11.2 | 11.6 |
| | Yield of 1224yd (%) | | 14.4 | 13.4 | 13.1 | 12.9 | 8.8 | 6.1 | 5.5 | 5.8 |

TABLE 2

| | | Compound (abbreviation) | | | | | | |
|---|---|---|---|---|---|---|---|---|
| | E1 | E2 | E3 | E4 | E5 | E6 | E7 | E8 |
| Composition of generation gas (mol %) | | | | | | | | |
| 1224yd(Z) | 5.20 | 4.71 | 5.29 | 3.23 | 4.74 | 3.12 | 2.05 | 1.95 |
| 1224yd(E) | 8.24 | 8.40 | 6.01 | 7.82 | 2.69 | 2.88 | 2.68 | 2.92 |
| 1214ya | 42.50 | 42.01 | 42.46 | 43.57 | 45.00 | 43.08 | 49.20 | 49.59 |
| HFO-1234yf | 38.50 | 39.55 | 41.35 | 39.79 | 38.86 | 43.40 | 36.09 | 35.65 |
| HFC-254eb | 4.05 | 3.24 | 3.18 | 1.68 | 6.91 | 4.53 | 5.59 | 5.14 |
| HFC-263fb | 0.22 | 0.30 | 0.29 | 1.37 | 0.38 | 1.64 | 2.51 | 2.65 |
| HFO-1243zf | 0.00 | 0.01 | 0.01 | 0.43 | 0.01 | 0.02 | 0.29 | 0.54 |
| Others | 1.29 | 1.78 | 1.39 | 2.12 | 1.41 | 1.33 | 1.59 | 1.56 |

As is seen from Table 1 and Table 2, in the examples 1 to 4 being Examples of the present invention, high results were obtained regarding the total of the selection rate X to 1224yd(Z) and the selection rate Y to 1224yd(E) and regarding the yield of 1224yd, as compared with the examples 5 to 8 in which the specific surface area of the palladium catalyst in the palladium catalyst-carrying carrier falls out of the range of the present invention. Among the examples 1 to 4, in the examples 1and 2 in which the specific surface area of the palladium catalyst in the palladium catalyst-carrying carrier was 6 to 20 m$^2$/g, especially high results were obtained regarding the total of the selection rate to 1224yd (Z) and the selection rate to 1224yd(E) and regarding the yield of 1224yd.

According to the production method of the present invention, in the method to obtain 1224yd by reducing 1214ya, it is possible to produce high-purity 1224yd by inhibiting the production of reduced products such as HFO-1234yf and HFC-254eb. Being low in global warming potential (GWP), 1224yd obtained by the method of the present invention is useful as a compound replacing chlorofluorocarbons for the application in a cleaning agent, a refrigerant, a forming agent, a solvent, and aerosol.

What is claimed is:

1. A method for producing 1-chloro-2,3,3,3-tetrafluoropropene, comprising:
reacting 1,1-dichloro-2,3,3,3-tetrafluoropropene with hydrogen in a gas phase in the presence of a palladium catalyst-carrying carrier in which a palladium catalyst having a specific surface area of 40 m$^2$/g or less is carried on a carrier.

2. The method according to claim 1, wherein the specific surface area is 6 to 33 m$^2$/g.

3. The method according to claim 1, wherein the specific surface area is 6 to 20 m$^2$/g.

4. The method according to claim 1, wherein the palladium catalyst contains palladium, and optionally a metal except palladium whose ratio to 100 parts by mass of palladium is 50 parts by mass or less.

5. The method according to claim 1, wherein a mass ratio of the palladium catalyst to the carrier is 0.1 to 10% by mass.

6. The method according to claim 1, wherein the palladium catalyst consists of palladium.

7. The method according to claim 1, wherein the carrier is an activated carbon.

8. The method according to claim 7, wherein the activated carbon is a palm shell activated carbon.

9. The method according to claim 1, wherein a ratio of the number of moles of a molecule of the hydrogen to the number of moles of the 1,1-dichloro-2,3,3,3-tetrafluoropropene is 1.4 or less.

* * * * *